United States Patent [19]

Michelson

[11] Patent Number: 4,693,717
[45] Date of Patent: Sep. 15, 1987

[54] INTRAOCULAR LENS FORMED IN SITU WITHIN THE EYE

[76] Inventor: Paul E. Michelson, 2280 Calle Tiara, La Jolla, Calif. 92037

[21] Appl. No.: 838,692

[22] Filed: Mar. 12, 1986

[51] Int. Cl.⁴ .............................................. A61F 2/16
[52] U.S. Cl. ...................................................... 623/6
[58] Field of Search ............................................ 623/6

[56] References Cited

U.S. PATENT DOCUMENTS

| | | | |
|---|---|---|---|
| 4,056,855 | 11/1977 | Kelman | 623/6 |
| 4,253,199 | 3/1981 | Banko | 623/6 |
| 4,268,921 | 5/1981 | Kelman | 623/6 |
| 4,373,218 | 2/1983 | Schachar | 623/6 |
| 4,449,257 | 5/1984 | Koeniger | 623/6 |
| 4,478,596 | 10/1984 | Michelson | 604/890 |
| 4,542,542 | 9/1985 | Wright | 623/6 |
| 4,585,457 | 4/1986 | Kalb | 623/6 |
| 4,619,662 | 10/1986 | Juergens, Jr. | 623/6 |

*Primary Examiner*—Ronald L. Frinks
*Attorney, Agent, or Firm*—Spencer & Frank

[57] ABSTRACT

A method of implanting an artificial lens within an eye. The method includes providing a collapsible lens mold comprised of a transparent, flexible sheath which defines a cavity bounded by opposite anterior and posterior portions of the sheath. The sheath portions are each preformed so that the cavity has a predetermined lenticular shape when the cavity is filled with a flowable material. The mold further includes a tubule connected to the sheath and communicating with the cavity for providing a conduit for a flowable material to be injected into the cavity. The mold is inserted in a collapsed condition into an eye so that the tubule is accessible to a tool for injecting a flowable material into the cavity. A lenticular material is provided which has a first state in which the material is flowable and a second state in which the material is shape retaining and has a desired refractive index. The material changes from the first state to the second state under conditions extant within the eye. The material is injected into the cavity of the sheath through the tubule until the cavity is filled. The material assumes the shape determined by the preformed portions of the sheath. Thereafter the material is allowed to change from the first state to the second state, thereby retaining the shape determined by the preformed portions of the sheath and forming an optical lens having a power determined by the shape of the sheath and the refractive index of the material.

4 Claims, 2 Drawing Figures

INTRAOCULAR LENS FORMED IN SITU WITHIN THE EYE

BACKGROUND OF THE INVENTION

The present invention concerns an intraocular lens which can be inserted into the eye through a relatively small incision on the order of 2 to 3 mm.

Since the development of the phacoemulsification technique by which a cataract can be removed through a small, 2 to 3 mm incision in the eye, there has existed the possibility of implanting an intraocular lens through such an incision. U.S. Pat. Nos. 4,056,855 and 4,268,921, both to Kelman, describe lenses which could fit through a relatively small incision, however, these and other variations have been limited by the diameter of a functional optic, i.e. the dimension of the lens used in passing and refracting light through the pupil. Until recently, a minimal functional diameter was felt to be 5.5 mm. Most intraocular lenses have a 6.0 mm diameter of the functional optic, and it has been deemed advisable by many to present an even larger optical zone for the overall visual efficiency of the eye.

Presently developed, approved, and time-tested lenses are made of a hard plastic composed of polymethylmethacrylate. Such material is not compressible and thus cannot be placed through an incision smaller than its diameter. Accordingly, other techniques and materials have been explored. For example Kelman has utilized a winged type of construction whereby a round, hard plastic implant can be inserted through a 3 mm incision, after which the round optic is expanded. However, this yields only a 3 mm clear zone centrally bounded by frosted wings on each side of the rectangular central optic.

Recently, Staar Surgical Company and Dr. Thomas Mazocco have initiated clinical trials with a silicone lens which can be folded through a 3 mm incision. U.S. Pat. No. 4,449,257 to Koeniger describes a lens made of hydroxyethylmethacrylate, a hydrogel, which can be inserted through a small incision in the eye and allowed to hydrate and enlarge a predetermined size and power within the eye.

U.S. Pat. No. 4,373,218 to Schachar and U.S. Pat. No. 4,478,596 to Michelson each describe an intraocular lens composed of a fluid-expandable sac which can be inserted in a dry, folded condition through a small incision and then inflated in situ within the eye by an optical fluid. In Michelson, the fluid-expandable sac is formed by a semipermeable sheath. A macromolecule having a size larger than the pores in the sheath are disposed within the sac for setting up an osmotic gradient which draws aqueous humor fluid from the anterior chamber of the eye through the pores of the semipermeable sheath into the sac for inflating the sac to a predetermined shape. In Schachar, on the other hand, the fluid-expandable sac is made of a nonporous material and is inflated in situ with either a liquid or a gas by way of a valve, or tubule, which communicates with the interior of the sac and extends through the sclera of the eye. One of the problems that can develop with the intraocular lens of both Michelson and Schachar is that if the sac should become ruptured, for example as a result of subsequent surgical or laser intervention to disrupt a clouded "secondary cataract" or residual posterior capsule of the natural lens, some or all of the fluid in the sac may be released, altering the optical power of the implanted lens.

U.S. Pat. No. 4,542,542 to Wright describes a method for replacing the lens of an eye which involves removing the natural lens, while retaining the natural lens capsule, and forming a synthetic lens in situ in the eye. This is accomplished by injecting into the natural lens capsule a synthetic lenticular composition which is initially pourable and which undergoes a physical change, in situ, due to a curing action which solidifies the composition. The synthetic composition conforms to the shape of the natural lens capsule and holds its shape upon solidification. Wright thus uses the natural lens capsule as a mold to form a synthetic lens in situ in the eye. Wright suggests that this in situ formation of a lens is an improved alternative to other intraocular lens implants because, among other things, it involves a less traumatic and faster surgical procedure. The use of the natural lens capsule to form the lens according to Wright, however, has the disadvantage that the configuration of the natural lens capsule cannot be changed and it is not possible to adjust the power of the in situ formed lens, although it may accommodate as the natural lens does in youth. Additionally, it is not always possible to remove a cataract without destroying part of the natural lens capsule. In such an instance, a synthetic lens formed according to Wright may not have desirable optical characteristics or be practical.

SUMMARY OF THE INVENTION

It is an object of the invention to provide an intraocular lens which has a larger optical section than heretofore available and which at the same time is insertable through a 2 to 3 mm incision in the eye.

It is a further object of the invention to provide a method for fabricating an intraocular lens in situ within the eye and which avoids the disadvantages discussed above of previously known methods for fabricating in situ intraocular lenses.

The above and other objects of the invention are accomplished according to the invention by the provision of a method of implanting an artificial lens within an eye, which method includes:

providing a synthetic, collapsible lens mold comprised of a transparent, flexible sheath which defines a cavity bounded by opposite anterior and posterior portions of the sheath, the portions each being preformed so that the cavity has a predetermined lenticular shape when the cavity is filled with a flowable material, the mold further including a tubule connected to the sheath and communicating with the cavity for providing a conduit for a flowable material to be injected into the cavity;

inserting the mold in a collapsed condition within an eye so that the tubule is accessible to a tool for injecting a flowable material into the cavity of the sheath via the tubule;

providing a lenticular material which has a first state in which the material is flowable and a second state in which the material is shape retaining and has a desired refractive index, the material changing from the first state to the second state under conditions extant within an eye;

injecting the lenticular material into the cavity of the sheath through the tubule until the cavity is filled, the material assuming the shape determined by the preformed portions of the sheath; and allowing the material to change from the first state to the second state, thereby retaining the shape determined by the preformed portions of the sheath and forming an optical lens having a power determined by the shape of the preformed portions of the sheath and the refractive index of the lenticular material.

According to a further aspect of the invention an intraocular lens is provided which includes a lens mold and an optical lens formed in situ within the lens mold in accordance with the method described above.

The intraocular lens formed according to the invention thus has the advantage of permitting the use a small, 2 to 3 mm incision created in the eye for the removal of a cataract to insert the sheath, comprising the lens mold, in a collapsed condition whereby the mold is subsequently inflated with a material which cures in situ to form an optical lens having a power determined by the preformed anterior and posterior portions of the sheath and by the refractive index of the material in its cured state. Should the sheath subsequently be ruptured, the optical lens, which in its cured state comprises a gel or solid, will maintain its configuration and thus will not suffer the deleterious effects of the previously known liquid or gas optical lenses formed within a flexible sheath. The intraocular lens formed according to the method of the invention also has the advantage over Wright in that by inserting a sheath having preformed anterior and posterior portions, the power of the lens is not limited by the shape of the natural lens capsule or by a requirement to maintain the integrity of the natural lens capsule during surgical removal of a cataract.

DESCRIPTION OF THE PREFERRED EMBODIMENT

Figure 1:
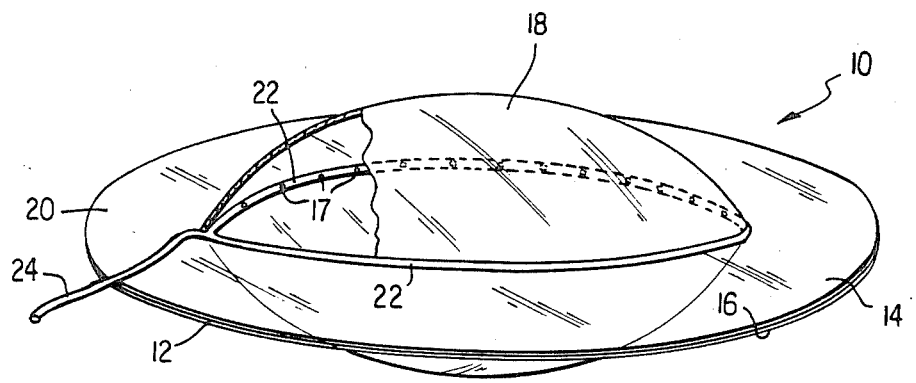
FIG. 1 is a perspective view, partially cut away, of an intraocular lens according to the invention.

Referring to FIG. 1 there is illustrated an intraocular lens arrangement 10 comprising a flexible sheath 12 composed of two transparent, film-like sheets 14 and 16 which are joined together to define a cavity 18 and an outer annular portion 20 which may constitute a haptic for centering and fixing the lens within a chamber of the eye. Cavity 18 is intended to be filled in situ with a material of desired refractive index constituting the lens. For this purpose there is provided at the inner circumference of cavity 18 a hollow tubule 22 which completely surrounds the cavity 18 and which communicates with a further tubule portion 24 which can be appropriately joined to haptic 20 for stability. Tubule 22 has a plurality of holes 17 via which a liquid or otherwise pourable material may be introduced into cavity 18 via tubules portion 22 and 24. The provision of a plurality of holes in tubule 22 permits the pourable material to be introduced into cavity 18 in an even manner. Alternatively, tubule 22 can be dispensed with and the pourable material can be simply introduced into cavity 18 via tubule member 24 which opens directly into cavity 18. The haptic 20 surrounding cavity 18 may takes on a variety of configurations. The provision of a haptic serves to stabilize the lens within the eye either in the posterior chamber, anterior chamber or within a lamellar pocket dissected into the substance of the cornea.

Figure 2:
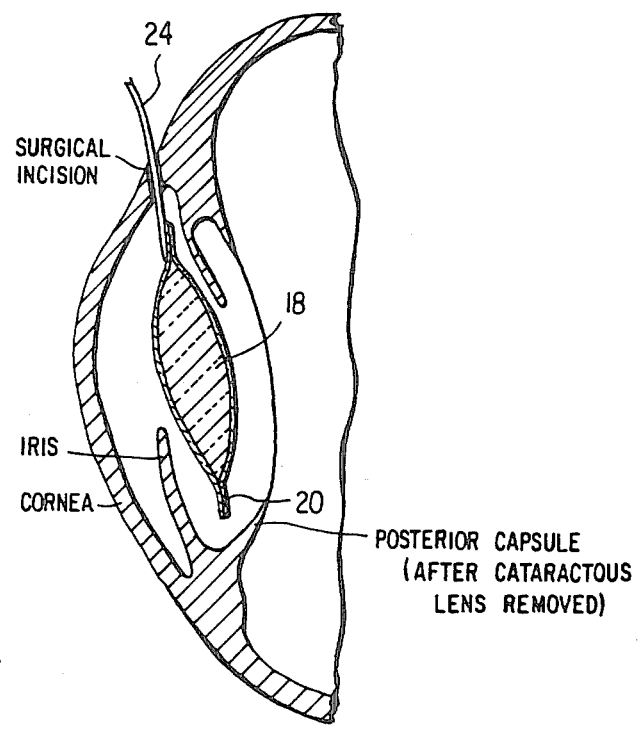
FIG. 2 is a schematic drawing showing an intraocular lens formed within a chamber of the eye according to the invention.

FIG. 2 shows an intraocular lens arrangement 10 according to the invention inserted into the posterior chamber of an eye. The sheath 12 is inserted in a collapsed condition through a small incision created in the sclera of the eye as described for example in Schachar (U.S. Pat. No. 4,373,218). As described in Schachar, the insertion of the collapsed sheath may be accomplished by folding the collapsed sheath into the end of a hollow needle, passing the end of the needle through the incision in the eye and forcing the folded sheath out of the needle via fluid pressure or a rod like instrument passing through the hollow portion of the needle or the sheath may be simply folded along an axis and inserted to expand in situ.

The thickness of each transparent, film-like sheet 14, 16 used for the sheath will depend on the factors and parameters related to the intended use of the lens. Each sheet will have its optical portion, i.e. the portion bounding cavity 18, preformed by known heat or vacuum techniques to desired specifications to provide predetermined posterior and anterior curvatures. In general, the film thickness will range from 5 to 10 micrometers. The sheet material may be porous or nonporous and can be chosen from a group of polymer films such as cellulose acetate, cellulose acetate butyrate, poly-14 butylene terephthalate, polyvinylidene chloride, other polymer or copolymer films or other transparent sheet material. Tubules 22 and 24 can be made of a medical grade silicone, polyethylene, or other suitable material. Such tubules have an outer diameter between 0.75 to 1.0 mm and an inner diameter of 0.50 to 0.80 mm. The two opposing sheets 14 and 16 of the sheath and the tubules can be joined together by various techniques well known in the art. For example, a variety of heat and impulse ultrasonic sealers can be used, with the specific parameters of temperature, frequency and time being selected depending upon the particular substances involved. Similarly, various one-part and two-part compatible adhesive bonding systems such as silicone adhesive, 3-M CONTACT CEMENT, EASTMAN 910, etc. can be used. Vinylidene chloride may be sealed to itself in the so-called "super-cooled" state without using conventional dielectric heat or adhesive methods, as understood by those skilled in the art.

A simple 1 to 2 mm wide cuff surrounding the optical portion of the lens and made up of the opposing sheet members of the sheath may well suffice for adequate centration and fixation of the intraocular lens, particularly if it is placed within the natural lens capsule after a cataract has been removed. If, on the other hand, the sheath is placed into a lamellar pocket dissected into the substance of the cornea, it may not be necessary to provide a haptic to assist in centration and stabilization of the lens, since the sheath would be inserted into the pocket via a small incision leading to the pocket and the pocket would simply be lined by the sheath.

In accordance with the invention the material injected into the cavity 18 of the sheath is characterized by the fact that it is a liquid or at least flowable in one state and will polymerize or gel to maintain its configuration under the environmental conditions extant within the eye. For example, a silicone gel with a refractive index of 1.41 may be formed by cross linking at body temperature from a 10:1 mixture of fluid polydimethyl vinyl-terminated siloxane and polymethylhydro, dimethylsiloxane. Other suitable lens materials, curable in situ, may be used for this purpose as disclosed, for example, in U.S. Pat. No. 4,542,542 to Wright. Once cavity 18 is filled to the desired level, tubule 24 is sealed by crimping or other suitable means, if necessary.

The following example is set forth as illustrative only, and is not intended in any way to limit the scope and purpose of the present invention.

Example: An intraocular lens may be constructed in accordance with the invention as a symmetrically, biconvex, intraocular lens having a power of 20 diopters with a refractive index of 1.4 and an optical zone having a diameter of 6.0 mm. The anterior radius and posterior radius of such a lens is thus 6.4 mm, creating a center lens maximum thickness of 2.4 mm. At the circumference of the useable optical portion of the sheath there is provided a silicone tube having an outer diameter of 1 mm and an inner diameter of 0.8 mm. One end of the tube is free outside of the sheath itself while one or more openings internal to the cavity of the sheath are provided so that the sheath can be filled with an appropriate lens material having a refractive index of 1.4. The sheath is vacuum formed from two polycarbonate sheets each having a thickness of 6.0 microns with a 2 mm, flat, circumferential cuff which will include the silicone circumferential tubule. The two sheets are bonded together along the circumferential cuff. The overall diameter of the lens is thus 10 mm. Prior to installation of the lenticular material itself into the cavity of the sheath, the sheath is folded upon itself in such a way as to be insertable through a 2.5 mm incision leading to a capsular bag of the eye from which a cataract has been extracted. After insertion of the sheath into the capsular bag, the lens material is injected through the free end of the tubule extending from the edge of the sheath and, if desired, through the incision of the eye. A predetermined amount of 10:1 liquid mixture of vinyl-terminated polydimethylsiloxane and polymethylhydro, dimethylsiloxane is injected until the sheath is inflated and no stress lines or distortions are evident in the optical portion.

Because of the small size of the incision, and lack of distortion of the cornea and remainder of the eye, the power in situ can then be corroborated using either automated or manual retinoscopy. Once the power is ascertained as desired, the free end of the tubule is crimped or otherwise sealed and inserted to the eye behind the iris, within the capsular bag, through an iridotomy or in any other convenient manner prior to closing the incision. The lenticular material injected into the cavity will then cure under the environmental conditions within the eye to form a gel which retains the shape of the preformed anterior and posterior portions of the sheath utilized with the optical portion of the lens.

Those skilled in the art will appreciate minor and obvious adaptations to the lens design and technique will allow fixation of the lens in the ciliary sulcus, to the iris, or within the pupil, or within the anterior chamber.

It will be understood that numerous modifications, changes and adaptations of the above description are intended to be comprehended within the meaning and range of equivalents of the appended claims.

What is claimed is:

1. A method of implanting an intraocular lens within an eye, said method comprising:

providing a collapsible lens mold comprised of two transparent, flexible, film-like sheets which are bonded together to form a sheath which defines a cavity bounded by opposite anterior and posterior portions of the sheath, said portions each being preformed so that the cavity has a predetermined lenticular shape when the cavity is filled with a flowable material, said mold further including a tubule connected to said sheath and communicating with said cavity for providing a conduit for a flowable material to be injected into said cavity;

inserting said mold in a collapsed condition into an eye so that said tubule is accessible to a tool for injecting a flowable material into the cavity of said sheath via said tubule;

providing a lenticular material which has a first state in which the material is flowable and a second state in which the material is shape retaining and has a desired refractive index, the material changing from the first state to the second state under conditions extant within the eye;

injecting said material, while in the first state, into the cavity of the sheath through the tubule until the cavity is filled, the material assuming the lenticular shape determined by the preformed portions of the sheath; and allowing the material to change from the first state to the second state, thereby retaining the lenticular shape determined by the preformed portions of the sheath and forming an optical lens within the sheath having a power determined by said lenticular shape and the refractive index of the material.

2. An intraocular lens including a synthetic lens arrangement mold and an optical lens formed in situ within the lens mold while in the eye according to the method of claim 1.

3. A method of implanting an artificial lens according to claim 1, wherein said step of providing a collapsible lens mold includes providing the tubule so that it surrounds the cavity and is provided with a plurality of openings through which the lenticular material can flow into the cavity during said injecting step.

4. An intraocular lens including a synthetic lens arrangement mold and an optical lens formed in situ within the lens mold while in the eye according to the method of claim 3.

* * * * *